(12) United States Patent
Mapoles et al.

(10) Patent No.: US 7,106,432 B1
(45) Date of Patent: Sep. 12, 2006

(54) SURFACE INSPECTION SYSTEM AND METHOD FOR USING PHOTO DETECTOR ARRAY TO DETECT DEFECTS IN INSPECTION SURFACE

(75) Inventors: Evan R. Mapoles, San Ramon, CA (US); Grace H. Chen, San Jose, CA (US); Christopher F. Bevis, Los Gatos, CA (US); David W. Shortt, Milpitas, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 201 days.

(21) Appl. No.: 10/315,713

(22) Filed: Dec. 9, 2002

Related U.S. Application Data

(60) Provisional application No. 60/414,206, filed on Sep. 27, 2002.

(51) Int. Cl.
 *G01N 21/00* (2006.01)
 *G01N 21/88* (2006.01)
 *G06K 9/00* (2006.01)

(52) U.S. Cl. .............................. 356/237.2; 356/237.1; 356/237.4; 356/237.5; 250/559.45; 382/149

(58) Field of Classification Search .. 356/237.1–237.5, 356/241.1–241.6, 238.1–238.3; 250/559.4–559.45; 382/141, 145, 144, 147, 148, 149; 348/125, 348/126, 128
 See application file for complete search history.

(56) References Cited

U.S. PATENT DOCUMENTS

| 4,173,415 | A | 11/1979 | Wyatt |
| 4,511,803 | A | 4/1985 | Röss et al. |
| 4,583,861 | A | 4/1986 | Yamaji et al. |
| 4,710,642 | A | 12/1987 | McNeil |
| 4,991,971 | A | 2/1991 | Geary et al. |
| 5,204,910 | A * | 4/1993 | Lebeau ........................ 382/152 |
| 5,790,251 | A | 8/1998 | Hagiwara |
| 5,798,831 | A | 8/1998 | Hagiwara |
| 6,034,776 | A | 3/2000 | Germer et al. |

(Continued)

FOREIGN PATENT DOCUMENTS

JP  2001281097 A  10/2001

OTHER PUBLICATIONS

U.S. Appl. No. 10/315,340, filed Dec. 9, 2002, Entitled: "Darkfield Inspection System Having Photodetector Array", Inventors: Bevis et al.

(Continued)

*Primary Examiner*—Gregory J. Toatley, Jr.
*Assistant Examiner*—Gordon J. Stock, Jr.

(57) ABSTRACT

A dark field surface inspection tool of the invention includes an illumination source for directing a light beam onto a work piece. The tool includes a scanning element for enabling selected inspection points on the work piece to be scanned by the light beam. During scanning, the light scattered by each inspection point generates light scattering patterns associated with the surface characteristics of the scanned inspection point. The tool includes a photo detector array having photosensitive elements arranged to receive light from the light scattering pattern, thereby capturing an image of the light scattering pattern for each inspection point. Comparison circuitry is included for comparing light scattering patterns with a reference image to enable the identification of defects at the inspection point. The invention also includes a dark field surface inspection method comprising illuminating an inspection surface with a light beam, capturing images of light scattered from the inspection surface and comparing those images with suitable reference images to detect defects in the inspection surface.

13 Claims, 9 Drawing Sheets

U.S. PATENT DOCUMENTS

| | | |
|---|---|---|
| 6,178,257 B1 * | 1/2001 | Alumot et al. ............... 382/145 |
| 6,259,521 B1 | 7/2001 | Miller et al. |
| 6,271,916 B1 | 8/2001 | Marxer et al. |
| 6,333,785 B1 * | 12/2001 | Schmolke et al. ....... 356/243.4 |
| 6,411,377 B1 * | 6/2002 | Noguchi et al. ......... 356/237.4 |
| 6,534,222 B1 | 3/2003 | Suzuki |
| 6,562,248 B1 | 5/2003 | Subramanian et al. |
| 6,603,541 B1 | 8/2003 | Lange |
| 6,621,568 B1 * | 9/2003 | Yonezawa ................ 356/237.2 |
| 6,661,912 B1 | 12/2003 | Taguchi et al. |
| 2003/0218741 A1 | 11/2003 | Guetta |
| 2004/0016896 A1 | 1/2004 | Almogy et al. |

OTHER PUBLICATIONS

Handbook of Optics, vol. 1, Fundamentals, Techniques, and Design, Second Edition, 1995, McGraw-Hill, Inc., pp. 30.4-30.8.

* cited by examiner

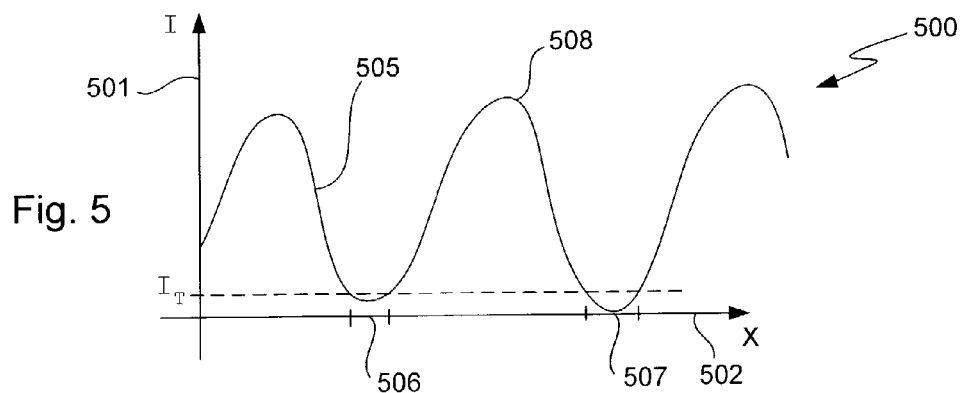
Fig. 5
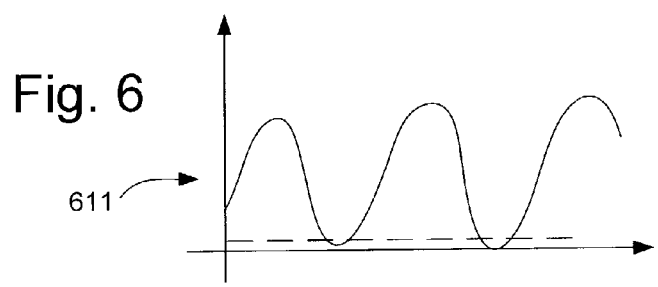
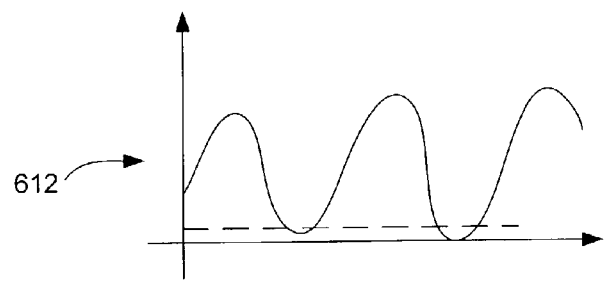
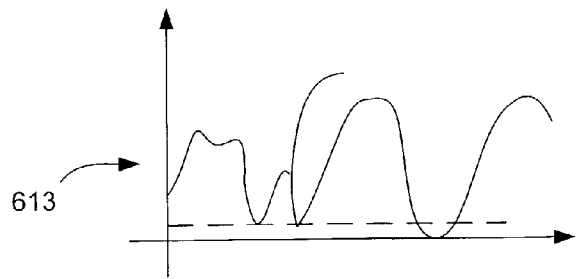
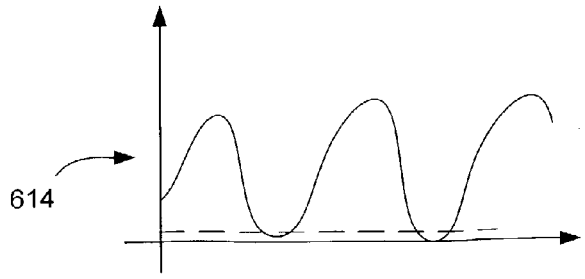
Fig. 6

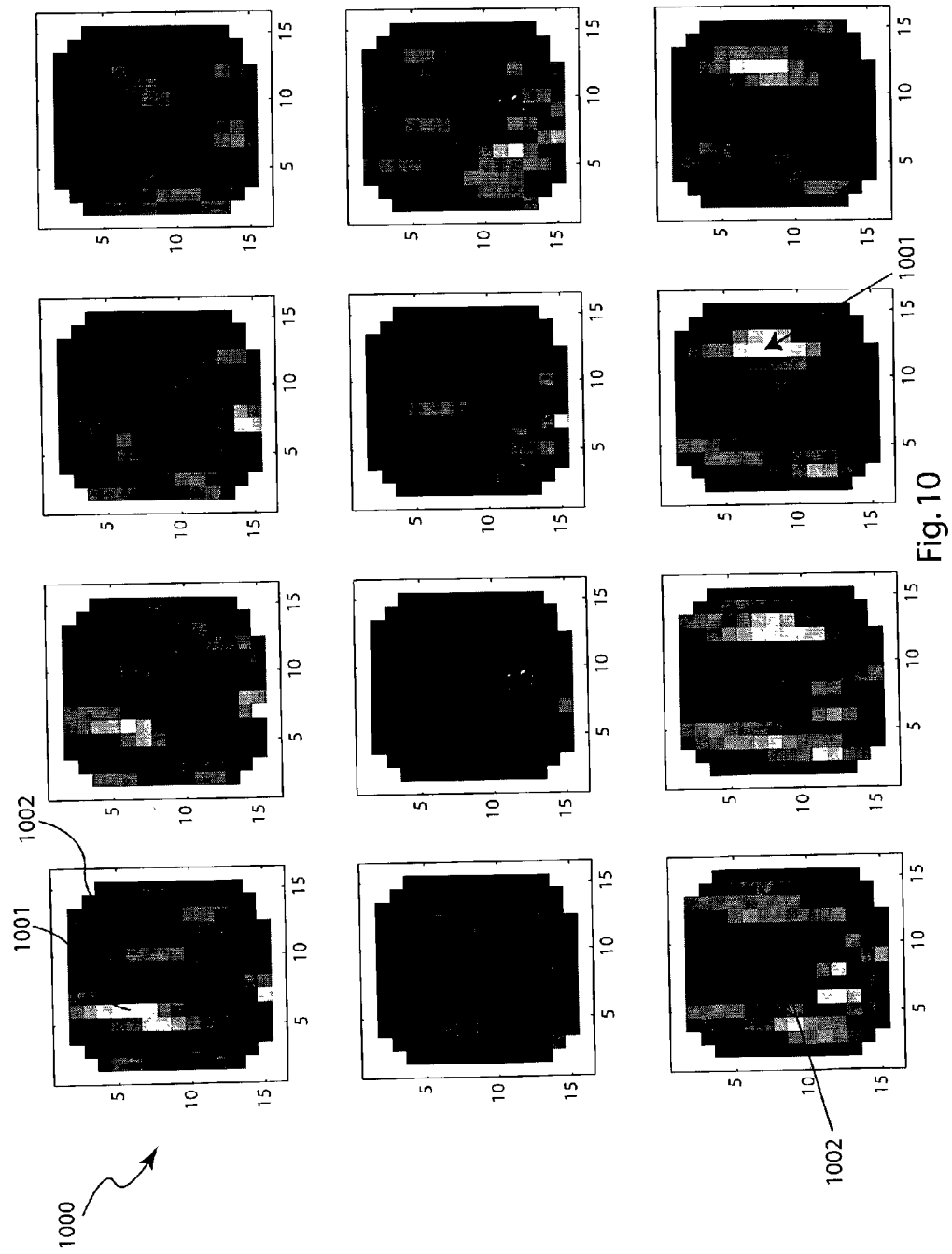

SURFACE INSPECTION SYSTEM AND METHOD FOR USING PHOTO DETECTOR ARRAY TO DETECT DEFECTS IN INSPECTION SURFACE

RELATED APPLICATIONS

This application is claims priority to U.S. Provisional Patent Application Ser. No. 60/414,206, entitled "Darkfield Inspection System Having Photodetector Array", by inventors Christopher F. Bevis et al., filed on Sep. 27, 2002 which is hereby incorporated by reference.

This application is related to the concurrently filed U.S. patent application 10/315,340 entitled "Darkfield Inspection System Having Photodetector Array", by inventors Christopher F. Bevis et al., which is hereby incorporated by reference.

TECHNICAL FIELD

The invention described herein relates generally to surface inspection and testing. In particular, the invention relates to devices and methods for dark field inspection of semiconductor wafer surfaces.

BACKGROUND OF THE INVENTION

For many years, dark field scanning methodologies have been used to scan surfaces. Dark field scanning makes use of light scattered by the surface features to characterize and examine features of the surface. FIG. 1 is a cross-section view of an illuminated surface used to illustrate aspects of dark field scanning. An illumination source 101 projects a light beam I (also referred to herein as the incident beam) onto the surface 102 being examined. A portion of the incident beam I is reflected by the surface as the reflected beam R. If the surface 102 was perfectly reflective, the entire incident beam I would be reflected. However, most surfaces have a variety of characteristics which cause a portion of the light from an incident beam I to be scattered. Dark field scanning makes use of this scattered light.

One particular surface feature that causes light scattering is referred to as a defect. The detection and quantification of defects are important in many areas. In particular, defect detection and analysis are important in semiconductor processing. In semiconductor processing, defects are frequently scattering features. Such defects typically occur in only one of the many dies on a wafer. Consequently, their detection is aided by systems that can compare the scattering patterns from multiple dies on a wafer and identify features which occur only in an isolated die. This method is called die-to-die comparison. Defects include, but are not limited to, pits, bumps, scratches, and a number of other features which mar the surface 102. Thus, the light of an incident beam I is often subject to some degree of scattering. FIG. 1 illustrates a typical incident beam I having a light scattering pattern schematically depicted by a plurality of scattered light rays 103, 104, 105, 106, and 107 which are scattered by a surface defect 108.

The dark field method places a single discrete light detector (not shown) so that it is not in the path of the reflected beam R. Thus, the background (the field) is dark. The scattered light received by the detector provides a representation of the surface 102 whereby the surface defects show up as lighter regions against the dark background or field. Hence, the name dark field scanning.

FIG. 2 is another cross-section view of a surface being scanned using dark field scanning. The surface 102 is illuminated by an incident beam I, a portion of which is reflected as reflected beam R. Another portion of the light of the incident beam I is scattered. Here, the scattered light is schematically depicted by the scattered light rays $S_1$, $S_2$, and $S_3$. Each of the scattered light rays $S_1$, $S_2$, and $S_3$ have scattering angles associated therewith. Because FIG. 2 is a two-dimensional representation of a three-dimensional reality, only one scattering angle is depicted for each of the scattered light rays $S_1$, $S_2$, and $S_3$. In the depiction of FIG. 2, the scattering angles are measured from the illuminated surface 102. Thus, scattered light ray $S_1$ is associated with scattering angle $A_1$. Scattered light ray $S_2$ is associated with scattering angle $A_2$. Scattered light ray $S_3$ is associated with scattering angle $A_3$, and so on. The scattering angles $S_1$, $S_2$, $S_3$ depicted here are determined from the surface 102. However, scattering angles can be described using other methods and coordinate systems. For example, the scattering angles can be determined from a line normal to the surface 102.

FIG. 3 is a schematic three-dimensional view of an incident light beam I and a scattered light ray 301. The depicted coordinate system is an x, y, z coordinate system with the surface lying in the x-z plane. One scattering angle is depicted as $\phi$, which is the angle from the x-z plane. The other depicted angle is $\theta$, which is the angle from the y-z plane. As was previously stated, many other ways of referring to scattered light ray angles are known and can be used.

One type of conventional dark field surface inspection device 400 is depicted in FIG. 4. An ellipsoidal mirror 420 is positioned over an inspection surface 402. An incident light beam 401 is directed onto an inspection surface 402. Schematically depicted are a reflected light beam 403 and many scattered light beams 410, 411, 412, 413, 414, 415, and 416. The device includes a first single discrete photodetector element 421 (for example a PMT) and a second discrete photodetector element 422 positioned above the ellipsoidal mirror 420. A portion of the scattered light (depicted here by scattered light beams 410, 411, 412, 413, 414, 415, and 416) passes through an opening 0 in the ellipsoidal mirror 420. The center portion of the scattered light beams (schematically depicted by beams 415, 416) passes through a lens 423, which directs the light onto a central mirror 424, which reflects the central beams 415, 416 so they converge at a side focal point 425. The second discrete photodetector element 422 is positioned at the side focal point 425 to receive the central beams 415, 416. At the same time, an outer portion of the scattered light beams (schematically depicted by beams 410, 411, 412, 413, 414) passes through the opening in the ellipsoidal mirror 420 and is reflected by the ellipsoidal mirror 420 onto a top focal point 426. The ellipsoidal mirror 420 is specifically designed to concentrate the outer portion of the scattered light beams 410, 411, 412, 413, 414 onto the top focal point 426. Also, the first discrete photodetector element 421 is specifically positioned at the top focal point 426. Frequently, the discrete photodetector elements 421, 422 include optical fibers that convey the focused light to a single discrete photodetector element (commonly, a single photo multiplier tube (PMT)). Such conventional discrete photodetector elements are commonly very sensitive to light intensity, but have no way of generating two-dimensional images that characterize scattered light from the inspection surface. Other related conventional approaches use discrete photodetector elements without the added optical fiber. By integrating light information from the first discrete photodetector element 421 and the second discrete photodetector element 422, the presence of a defect can be determined.

A problem with such discrete photodetector element systems is that they have difficulty discerning defects in patterned surfaces. Frequently, when patterned surfaces (e.g., the patterned surfaces of semiconductor wafers) are scanned, the resulting scattering pattern is detected as a "defect" by the discrete photodetector element. Even in systems which employ die-to-die comparison, small variations in the surface pattern and the resulting variation in scattering can mislead the system into falsely identifying a defect. Thus, portions of the (otherwise defect-free) patterned surface give false readings, as if they had defects in the surface. Conventional devices have attempted to circumvent this problem by so-called Fourier filtering. Under plane wave illumination, the intensity distribution at the back focal plane of a lens is proportional to the Fourier transform of the object. Further, for a repeating pattern, the Fourier transform consists of a pattern of light areas which remain constant as the wafer is scanned. By placing a filter in the back focal plane of the lens, these areas can be blocked (filtered). Thus, artifacts of the repeating circuit pattern can be filtered out and leave only non-repeating signals from particles and other defects. Such Fourier filtering is a common technology employed in wafer inspection machines from many manufacturers.

One of the limitations of Fourier filtering based instruments is that they can only inspect areas with repeating patterns (for example, arrays of memory cells) or blank areas. Critically, Fourier filtering of the type describe is not useful for inspecting non-uniform surfaces like random logic areas. These are some fundamental limitations of the technology.

For example, in the Hitachi Model IS-2300 inspection machine, darkfield Fourier filtering is combined with die-to-die image subtraction to effectuate wafer inspection. Using this technique, non-repeating pattern areas on a wafer can be inspected by the die-to-die comparison. However, even with such die-to-die comparison, conventional technologies still need Fourier filtering to obtain good sensitivity in the repeating array areas. For example, in dense memory cell areas of a wafer, a darkfield signal from the circuit pattern is usually so much stronger than that from the circuit lines in the peripheral areas that the dynamic range of the sensors are exceeded. As a result, either small particles in the array areas cannot be seen due to saturation, or small particles in the peripheral areas cannot be detected due to insufficient signal strength. Fourier filtering equalizes the darkfield signal so that small particles can be detected in dense or sparse areas at the same time.

Common disadvantages to such techniques include the following limitations. First, such machines can detect particle defects relatively well, but their sensitivity to pattern defects is very poor. Second, since the filtered images are usually dark without circuit features, it is not possible to do an accurate die-to-die image alignment, which is necessary for achieving good cancellation in a subtraction algorithm. One solution is to use an expensive mechanical stage of very high precision, but even with such a stage, due to the pattern placement variations on the wafer and residual errors of the stage, the achievable sensitivity is limited roughly to particles that are 0.5 µm and larger. This limit comes from the alignment errors in die-to-die image subtraction. Additionally, the filtering makes it difficult to detect defects in certain regions of the surface. Moreover, as surface patterns become more complicated (as is the case in modern VLSI circuit structures), the patterns become more complex, and more filtering must be implemented. As a result, less and less of the surface can be effectively scanned for defects. Additionally, although Fourier filtering can be extremely effective in filtering light scattered by array areas (e.g., memory cells), there is currently no similar technique that can be applied to areas of the wafer where the surface pattern is not regular and repeating. Examples of such areas include random logic areas. In these areas, the scattering pattern at the Fourier transform plane of a lens is not constant as the wafer is scanned. As a result, it is no longer practical to insert a fixed filter to selectively block light scattering caused by the surface pattern.

What is needed are dark field inspection tools and methodologies that can achieve adaptive filtering of surface pattern effects and address some of the foregoing difficulties.

BRIEF SUMMARY OF THE INVENTION

In accordance with the principles of the present invention, dark field inspection tools and methodologies are disclosed.

One embodiment of the invention includes a dark field surface inspection tool with an illumination source for directing a light beam onto a work piece. The tool includes a scanning element for enabling selected inspection points on the work piece to be scanned by the light beam. During scanning, the light scattered by each inspection point generates light scattering patterns associated with the surface characteristics of the scanned inspection point. The tool includes a photo detector array comprised of photosensitive elements arranged to receive at least some of the light from the light scattering pattern, thereby capturing an image of the light scattering pattern for each inspection point. Additionally, comparison circuitry is included for comparing the image of the light scattering pattern for each inspection point with a reference image that corresponds to the same inspection point to enable the identification of defects at the inspection point.

The invention also includes surface inspection methods. In one method embodiment, an inspection surface having a semiconductor die formed thereon is provided. An inspection point on the semiconductor die is scanned with a light beam to generate a light scattering pattern associated with the surface characteristics of the inspection point. A two-dimensional image of the light scattering pattern generated by the inspection point is captured, at a light detection surface, such that the intensity of the scattered light and the two-dimensional position of the scattered light are captured as an image. The two-dimensional image of the scattering pattern from the inspection point is compared with a reference image that corresponds to the same inspection point, said comparison enabling the identification of defects at the inspection point.

These and other aspects of the present invention are described in greater detail in the detailed description of the drawings set forth hereinbelow.

BRIEF DESCRIPTION OF THE DRAWINGS

The following detailed description will be more readily understood in conjunction with the accompanying drawings, in which:

FIG. 1 is a cross-sectional view showing an incident light beam being scattered from a semiconductor wafer surface.

FIG. 2 is a cross-sectional view showing an incident light beam being scattered from a semiconductor wafer surface and showing scattering angles for scattered light beams.

FIG. 3 is three-dimensional perspective view of scattering angles for a light beam being scattered from a surface.

FIG. 5 is graphical depiction of a simplified light intensity pattern generated by a die formed on an inspection surface.

FIG. 6 shows a comparison of four light intensity patterns associated with four different dies.

FIG. 10 shows a typical stream of images taken of light scattering patterns produced as a light beam is scanned across an inspection surface in accordance with the principles of the present invention.

It is to be understood that, in the drawings, like reference numerals designate like structural elements. Also, it is understood that the depictions in the Figures are not necessarily to scale.

DETAILED DESCRIPTION OF EMBODIMENTS OF THE INVENTION

Figure 1:
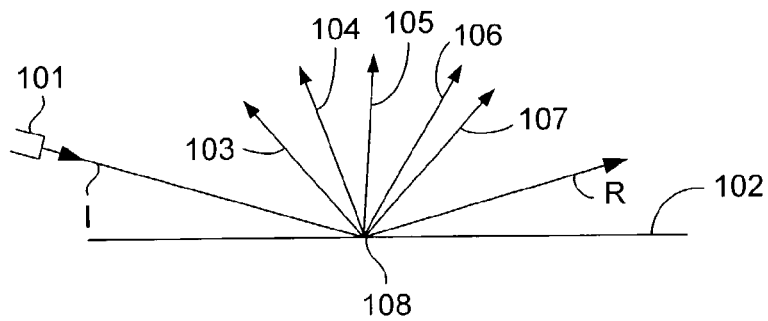
FIGS. 1–3 illustrate aspects of light scattering used in dark field inspection tools.
Figure 2:
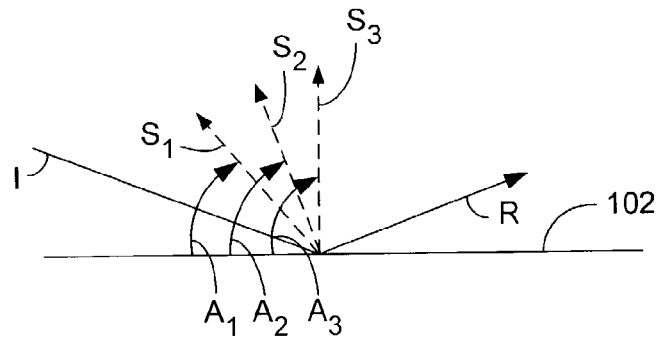
Figure 3:
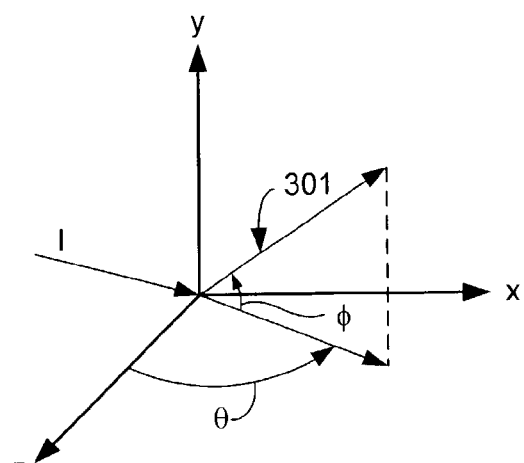
Figure 4:
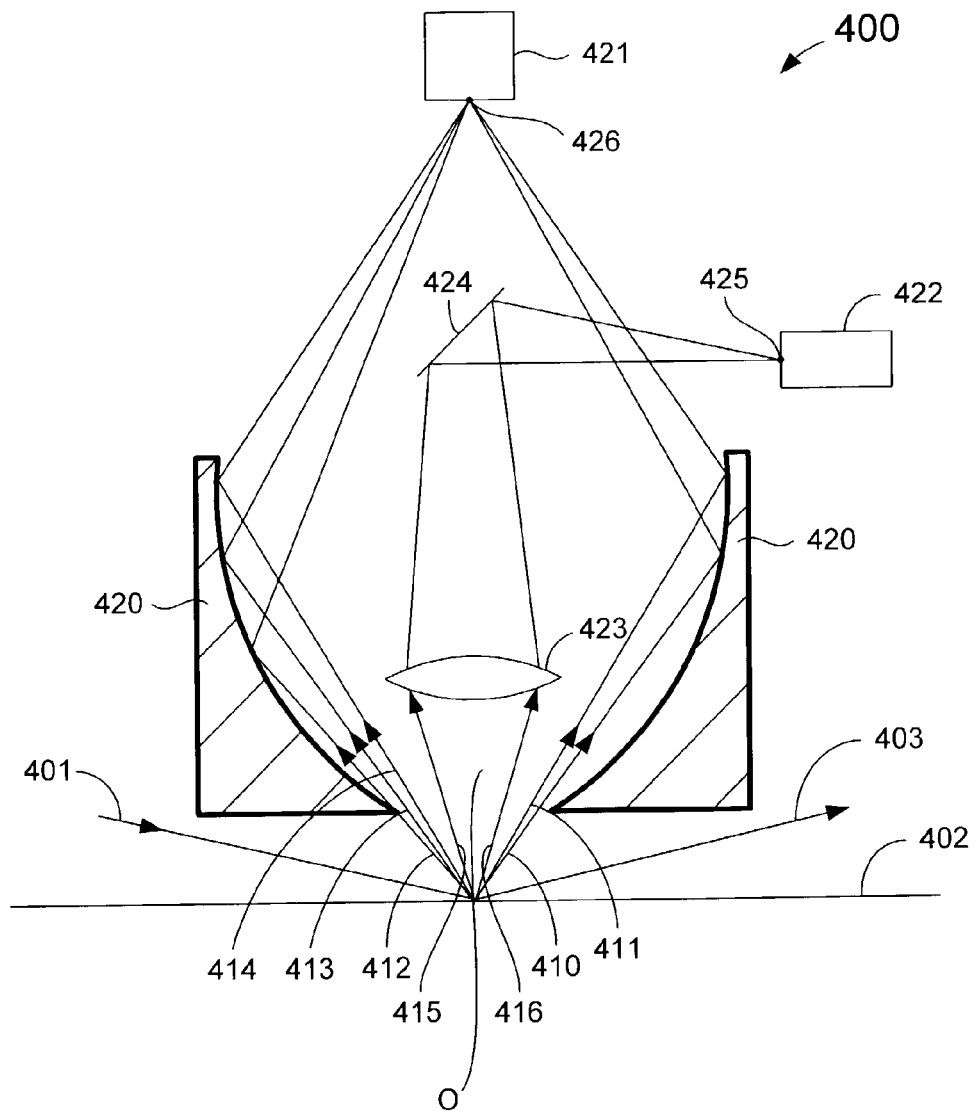
FIG. 4 is a cross-sectional view of one type of conventional dark field scanning apparatus.

The present invention has been particularly shown and described with respect to certain embodiments and specific features thereof. The embodiments set forth herein below are to be taken as illustrative rather than limiting. It should be readily apparent to those of ordinary skill in the art that various changes and modifications in form and detail may be made without departing from the spirit and scope of the invention.

FIGS. 5 and 6 are used to provide a simplified explanation of some of the basic principles of the invention. A patterned inspection surface is provided for inspection. The inspection surface can comprise many different surfaces. But, in most common implementations inspection surfaces comprise semiconductor substrates having a plurality IC die patterns formed thereon or mask reticles having a mask pattern formed thereon. Such mask patterns commonly include a mask pattern for forming a plurality IC dies. Typically, the inspection surface is patterned having a plurality of substantially identical semiconductor die patterns formed thereon. A typical inspection surface contains dozens of such dies. Because each die is patterned, light reflected, diffracted, and scattered from its surface has varying degrees of intensity. As a light beam is scanned over a die and light scattered from the surface is detected, a light intensity pattern emerges. FIG. 5 depicts a very simplified two-dimensional graph 500 of a light intensity pattern 505 (also referred to as a scattering pattern), plotting light intensity 501 versus the location 502 on a die producing the scattered light. As can be seen, there are regions having relatively high light intensity (light regions) 508 and regions having relatively low light intensity (dark regions) 506, 507. Dark regions are those regions where the light intensity falls below some intensity threshold $I_T$. In the depicted example, regions 506 and 507 are dark regions. If each die inspected were perfectly identical, each light intensity pattern 505 would also be identical. In practice, the light intensity patterns are commonly very similar. The presence of defects can cause a light intensity pattern to vary. Over many portions of the light scattering pattern, such variations in light intensity are difficult to detect. In particular, variations in light intensity are difficult to detect in the lighter regions 508 of the detected scattering pattern 505. However, because the dark regions (e.g., 506, 507) are black (or very nearly black), small variations in these regions can be detected by the increased amounts of light. These increased amounts of light are relatively easy to detect and can be used to identify defect candidates.

This principle is well illustrated in FIG. 6, which shows four sample light intensity patterns (611, 612, 613, and 614) associated with four different dies. Each of the light intensity patterns (611, 612, 613, and 614) was produced by scanning the same region of different dies located on the same inspection surface. The patterns of dark regions look substantially the same for light intensity patterns 611, 612, and 614. Notably, light intensity pattern 613 has a light spike 620 in a normally dark region. This indicates that the portion of the surface associated with the light spike 620 may have a defect located thereon. Thus, a direct die-to-die comparison can be used to detect the defect and conventional Fourier filtering is not required to detect defects in accordance with the principles of the present invention. This basic concept is expanded and further elucidated in the paragraphs below, which describe methods and apparatus for identifying and locating defects in inspection surfaces.

Generally, aspects of the invention are directed to surface inspection tools and method for their use. The tools typically include an illumination source for directing a light beam onto a work piece. A scanning element enables selected inspection points on the work piece to be scanned by the light beam. Light scattered by each inspection point generates light scattering patterns associated with the surface characteristics of each inspection point. These scattering patterns are detected by a photo detector array that comprises many photosensitive elements. The array captures images of the light scattering pattern for each inspection point. Comparison circuitry is included for comparing the images of the light scattering pattern for each inspection point with a reference image that corresponds to the same inspection point to enable the identification of defects at the inspection point. Additionally, the comparison circuitry can be used to generate the reference images.

One advantage of such an implementation is that it can be used to scan for defects in the heretofore difficult to inspect random logic areas on an inspection surface. Since the photodetector array captures an image of the scattering pattern from each scanned inspection point on a plurality of dies, a normal scattering pattern (unaffected by the presence of defects) can be determined. The bright areas of the normal scattering pattern can be mapped. In accordance with the scattering pattern certain photosensitive elements (pixels) are illuminated by the scatting pattern whereas other pixels are dark. Defects can then be located by examining the dark pixels for light variation. In fact, once a reference image is obtained for an inspection point the process can be made even more efficient by examining only the dark pixels.

This process is advantageous because it can be used to detect defects in areas of the inspection surface characterized by non-regular surface features (e.g., random logic areas). Ordinarily defects are very difficult to characterize in such areas using conventional techniques (e.g., Fourier filtering). Moreover, the technique can also detect defects in array structures using the same methodology.

As stated above, in some implementations, the methodology can be made extremely efficient by obviating the need to detect, measure, examine, and compare bright pixels. Such implementations are focused on the "dark" pixels of the reference image. And the pixels that detect the bright regions of the scattering pattern can be ignored. This is efficient both computationally and from data transfer point of view. Also, algorithms can be employed that identify the "darkest" subset of pixels of the photo detector array in the reference die by setting any pre-determined threshold for "darkness". Such filtering can be used to detect defects more effectively under certain noisy conditions. By examining only such "darkest" subset of pixels, the benefits of Fourier filtering in array areas can be extended to random logic areas.

The following detailed description describes various embodiments of dark field inspection tools and methods for their use. In particular, embodiments of the present invention include an illumination source for directing a light beam onto an inspection surface to create scattered light profiles associated with the surface characteristics of the inspection surface. Such surface characteristics include without limitation, variations in surface topography and variations in optical properties (e.g., refractive index) of the materials of the surface. Among the more common surface characteristics giving rise to scattering profiles are so-called phase shift structures coming in to wider usage. A scanning element moves either the beam or the inspection surface so that the beam scans a path across all the desired surfaces of the inspection surface. The resulting scattered light from the surface is received by the photosensitive elements (pixels) of a photo detector array where it is collected and used to generate images which can be used to characterize the inspection surface.

Figure 7:
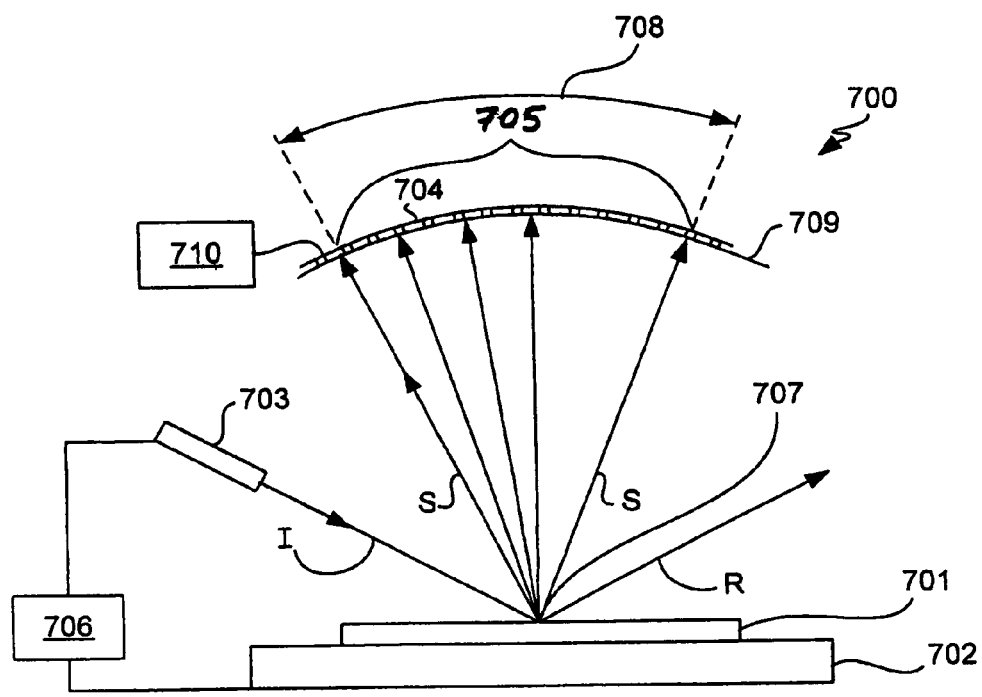
FIG. 7 is an illustration depicting a solid angle in accordance with the principles of the present invention.

FIG. 7 depicts a device 700 embodiment designed to inspect desired portions of an inspection surface (work piece) 701. As used herein, work pieces 701 refer to any inspected surface. Typical work piece examples include, but are not limited to, semiconductor wafers and pattern masks. The embodiments of the invention have particular utility when used on patterned work pieces 701. In use, the work piece 701 is typically positioned on a support 702, such as an electrostatic chuck or other commonly used apparatuses used for such purposes. An illumination source 703 directs a light beam I onto the work piece 701 generating a reflected beam R and creating scattered light beams S, which are received by photosensitive elements 704 of a photo detector array 705.

A scanning element 706 moves the work piece 701 and light beam I relative to one another so that the beam I scans a desired path over the surface of the work piece 701. During inspection, the light beam I illuminates specific inspection points (here inspection point 707) on the work piece 701 generating a light scattering pattern. The photo detector array 705 captures images of light scattering patterns generated as the beam I scans a desired path over the workpiece 701 surface. The photo detector array 705 is electrically connected to signal processing circuitry 710, which can receive image data from the photo detector array 705. The circuitry 710 can perform a number of electronic processes on the image data. Typically, such processes include, but are not limited to, image storage, image filtering, data analysis and comparison, as well as other image processes known to those having ordinary skill in the art.

The illumination source 703 depicted in FIG. 7 is a laser. In one implementation, the laser is an argon (Ar) ion laser. Such lasers typically emit light beams having wavelengths ($\lambda$) of 365 nm (nanometers), 488 nm, 532 nm, as well as other wavelengths. Additionally, such laser light beams produce a light dot having a spot size on the surface of the work piece. The light dots can be circular or ellipsoidal. As is also known to persons having ordinary skill in the art each illumination source 703 is characterized by an illumination solid angle. As is also known to persons having ordinary skill in the art, the illumination solid angle is related to the spot size of the system. Spot sizes typically range from about 10 microns ($\mu$) down into the sub-micron range. One common implementation is an elliptical light dot having a spot size of about $3\mu$ along the minor axis and about $10\mu$ along the major axis. Another common implementation is a circular light dot having a spot size of about $3\mu$ in diameter. Light dots are scanned across the surface of the work piece in a desired pattern enabling the desired portions of the surface to be inspected. Such scanning is accomplished using a scanning element 706 that can comprise a wide variety of scanning devices known to persons having ordinary skill in the art. Suitable scanning elements 706 include, but are not limited to, devices that scan the beam I across the work piece 701 by moving the work piece 701 relative to the light beam I. In other implementations, the scanning element moves the light beam I relative to the work piece 701 thereby scanning the beam I across the surface of the work piece 701. In some other implementations, the beam I can be moved by moving the illumination source 703 relative to the work piece 701. In another alternative embodiment, the beam I is directed onto a moving mirror, or array of mirrors, to direct the beam I onto the work piece 701 in a desired inspection pattern. As is known to those having ordinary skill in the art, many other implementations of scanning elements can be used in accordance with the principles of the present invention.

Still referring to FIG. 7, the photosensitive elements 704 of a photo detector array 705 are arranged along a detection surface 709. One example of a suitable detection surface 709 is a Fourier plane. In the depicted embodiment, the photosensitive elements 704 of a photo detector array 705 are arranged in a substantially hemispherical configuration about the inspection point 707. As is known to those having ordinary skill in the art, other arrangements are possible. In the depicted preferred embodiment, the photosensitive elements 704 of a photo detector array 705 are each sized so that they are about the same size as or smaller than the illumination solid angle for the source 703. Additionally, there should be enough photosensitive elements 704 such that the images include enough "dark" pixels (commonly about five or more). Preferably, such arrays include 100 or more photosensitive elements (e.g., 10×10 photo arrays). However, in theory, an array of 2×2 pixels is sufficient under the right conditions. However, one preferred implementation uses arrays having, for example, 256 pixels (photosensitive elements 704). Of course the minimum solid angle subtended by a photo detector array 705 is determined by the size and number of photosensitive elements 704 comprising the photo detector array 705. Factors like the spot size, wavelength of illuminating light, the illumination solid angle, fabrication constraints on minimum pixel size, as well as other factors play a role in the solid angle subtended by the photo detector array 705. In one example implementation, the photosensitive elements 704 of the photo detector array 705 are arranged so that they subtend a solid angle 708 of greater than about 40° (angular degrees) by 40°.

Thus, in one embodiment a photo detector array 705 is configured such that the photosensitive elements 704 of a photo detector array 705 are arranged about an inspection point 707 to cover a solid angle of greater than about 40° by 40°. The photo detector array 705 can be arranged having solid angles of less than 40° by 40°, but such arrangements are generally less effective at adaptive Fourier filtering because fewer dark regions are captured by the photo detector array 705.

As depicted in FIG. 7, the individual photosensitive elements 704 of a photo detector array 705 can be formed of a number of light sensitive detector devices including, without limitation, photodiodes, photo multiplier tubes (PMT's), charge-coupled devices (CCD's), CMOS detectors, and a variety of other light sensing devices known to those having ordinary skill in the art. As previously discussed, the photosensitive elements 704 are sized so that they subtend solid angles on the order of the illumination solid angle for the illumination source. As is known to persons having ordinary skill in the art such illumination solid angle is related to spot size. In preferred embodiments, each of the photosensitive elements 704 has a size that is related to the $\lambda$ of the incident light beam and the spot size for the light beam. In one implementation, each of the photosensitive elements 704 is configured such that it subtends an angle defined by the $\lambda$ of the incident light beam divided by the spot size for the light beam ($\lambda$/spot size). For example, using a laser having a $\lambda$ of 532 nm, and a spot size of 3$\mu$ in diameter, the angle is defined as 0.532/3 radians or about 10.2°. Thus subtending a solid angle of about 10.2° by 10.2°. However, as with all such optical systems, there is a trade off between sensitivity (lots of samples) and speed. Thus, in preferred implementations using a 3$\mu$ spot size, suitable solid angles can range from about 1.75° to 4°. However, a wider range of sizes for photosensitive elements 704 can be employed such that they subtend angles in the range of about 1.5° to about 12°. As can be appreciated by those with ordinary skill in the art, the actual size of the photosensitive elements 704 is determined by a number of factors, including, but not limited to $\lambda$ of the light, spot size, illumination solid angle, and distance the photosensitive elements are away from the inspection surface.

With continuing reference to FIG. 7, light from the beam I is directed onto the work piece 701 where it scatters as a plurality of scattered light beams S forming a light scattering pattern associated with the surface characteristics of the work piece 701. These beams S are detected and captured as images by the photo detector array 705. The photo detector array 705 can be used to capture images of the scattering pattern for each illuminated inspection point 707 on the work piece 701. These images comprise patterns of light and dark regions that can be compared with each other or with a reference image to locate defects. Reference images can be generated from die-to-die comparison or by using a digital model of the optical light scattering performance generated from a database model of the workpiece.

Figure 8:
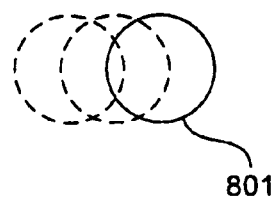
FIG. 8 depicts a laser dot being scanned across an inspection surface in accordance with the principles of the present invention.

An implementation of the principles of the invention used to locate defects is described in the following paragraphs. FIG. 8 depicts one embodiment of a scanning light dot 801. The depicted light dot 801 is circular, having a spot size of about 3$\mu$ in diameter. In one embodiment, the dot 801 is scanned over the surface of the work piece in 1$\mu$ increments. This is depicted in FIG. 8, which depicts each of the incremental movements of the dot 801 (depicted by the dashed dots) as it is scanned across the surface of the work piece. As the dot advances from one position to another, an image is taken of the light scattered from the work piece. Each of these images corresponds to a discrete inspection point on the surface of the work piece. As is known to those having ordinary skill in the art, the invention can be practiced using many different scanning patterns to inspect a surface.

Figure 9:
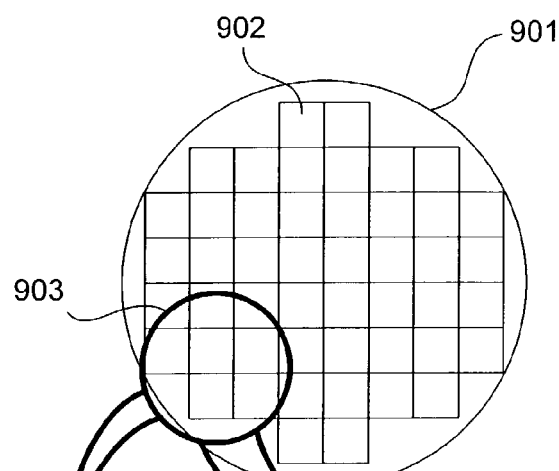
FIG. 9 is a plan view of a semiconductor wafer with a plurality of semiconductor dies formed thereon.

To further illustrate how these images can be used to detect defects, reference is hereby made to FIG. 9. FIG. 9 is a plan view that depicts an example work piece. As previously explained, a wide variety of work pieces can be inspected in accordance with the principles of the present invention. The depicted work piece is a semiconductor wafer 901 having formed thereon a plurality of substantially similar semiconductor dies 902. The depicted circle 903 encloses a plurality of semiconductor dies 902. As the light beam is scanned over the semiconductor wafer 901, an image can be taken for each inspection point (or a subset of inspection points). Images corresponding to the same inspection point on a plurality of dies can then be compared to identify defects.

As a light beam is scanned over the semiconductor wafer 901, a stream of images capturing the various scattering patterns can be generated. Electronic circuitry can be used to capture, store, or otherwise process this information.

FIG. 10 shows one example of a stream of sample images 1000 taken of scattering patterns as the light beam is scanned across a wafer. The depicted image stream is detected using a 16×16 photo detector array having 256 photosensitive elements. This photo detector array is used to capture sample images of each scattering pattern for each inspection point. FIG. 10 shows a series of 12 sample images captured sequentially as a light beam is scanned across the wafer. The depicted sample images 1000 each comprise patterns of light regions 1001 and dark regions 1002. It is noted that these patterns of light regions 1001 and dark regions 1002 are analogous to the light intensity patterns of FIGS. 5 and 6. Using concepts similar to that explained with respect to FIGS. 5 and 6, such patterns of light regions 1001 and dark regions 1002 can be used to identify defects in the wafer surface. In the absence of defects, a similar stream of sample images taken from equivalent locations on another die should appear nearly identical to the depicted image stream. Differences in the image streams can be used to identify points on the inspected surface that may have defects.

In one embodiment, patterns of dark regions taken from the same relative location on a plurality of dies can be compared to locate defects. In the absence of defects, each of the images for the same location on a plurality of different dies should look substantially the same. Thus, most images for the same location should have the same pattern of dark regions. Since most images are defect-free, these similar patterns of dark regions can be used as a reference pattern. If there were no defects in any of the inspection points, each of the images for the inspection points will look substantially the same (within some predetermined tolerance). If the pattern of dark regions in some images is lighter than an analogous pattern of dark regions in a reference image, the inspection points associated with those images can be identified as defect candidates. These candidates can be subjected to further analysis with other inspection methods and tools.

Figure 11:
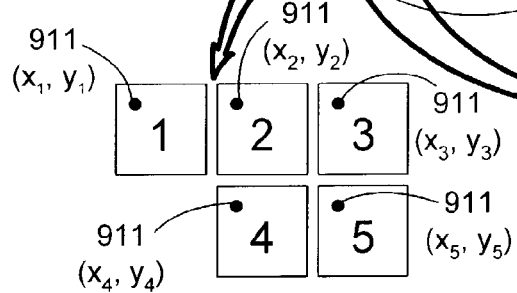
FIG. 11 is an expanded view of a portion of the wafer depicted in FIG. 9 showing the same inspection point on a plurality of different dies.

The above concepts can be better understood with reference to the following drawings and description. FIG. 11 is a close-up view of a portion 903 of the semiconductor wafer 901 depicted in FIG. 9. As a light beam is scanned across the semiconductor wafer 901, a series of inspection points is illuminated. As explained, an image is generated for each inspection point of interest. In a die-to-die comparison, the images produced for each inspection point on a die can be compared to the images produced for an analogous inspection point on every other die on the wafer 901.

FIG. 11 shows five substantially similar dies (1, 2, 3, 4, and 5) formed on the wafer 901. Each die is scanned as part of a scanning pattern that includes a series of inspection points. A two-dimensional image is generated for each inspection point. These images can be compared to locate defects. Each die is shown with a first inspection point 911 depicted (indicated by the dots). Each inspection point 911 corresponds to the same relative location (x, y) (e.g., for die 1 location $x_1$, $y_1$, for die 2 location $x_2$, $y_2$, for die 3 location $x_3$, $y_3$, and so on) on each other die of the wafer. Of course, the indicated inspection points 911 represent only one of many millions of possible inspection points on each die. The images generated by each first inspection point 911 can be compared with images for a corresponding inspection point 911 on each other die (or alternatively, to a database generated reference image) to find images having light in the dark patterns. Alternatively, the images generated by each first inspection point 911 can be compared with other images for a corresponding first inspection point 911 on other dies to generate a reference image for comparison with all of the first inspection points 911. Such reference image can be used to detect defects in the first inspection point 911.

Figure 12:
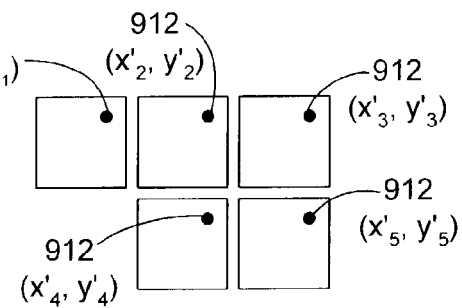
FIG. 12 is another expanded view of a portion of the wafer depicted in FIG. 9 showing another inspection point on a plurality of different dies.

During scanning of the entire wafer, as each die is scanned, additional inspection points are illuminated and images are taken of these scattering patterns. FIG. 12 shows the same die pattern depicted in FIG. 11 (e.g., dies 1, 2, 3, 4, and 5) with another different group of inspection points 912 depicted. In the depicted embodiment, each inspection point 912 corresponds to the same relative location (x', y') (e.g., for die 1 location $x_1'$, $y_1'$, for die 2 location $x_2'$, $y_2'$, for die 3 location $x_3'$, $y_3'$, and so on) on each die. Thus, images captured from these inspection points refer to a different location on the die. Thus, these images can be used to locate defects in inspection point 912 and the analogous inspection points on the other dies.

Once the images are captured by the photodetector array, they are processed by the electronic circuitry of the device. Such processing can include storage, filtering, data manipulation, and a host of other data processing operations known to those having ordinary skill in the art. In one embodiment, all of the images taken for the same inspection point on a plurality of dies can be analyzed together to detect defects for that inspection point. Such captured images can processed as a stream of images such that each image in the stream is associated with the same inspection point on a plurality of inspected dies.

Figure 13:
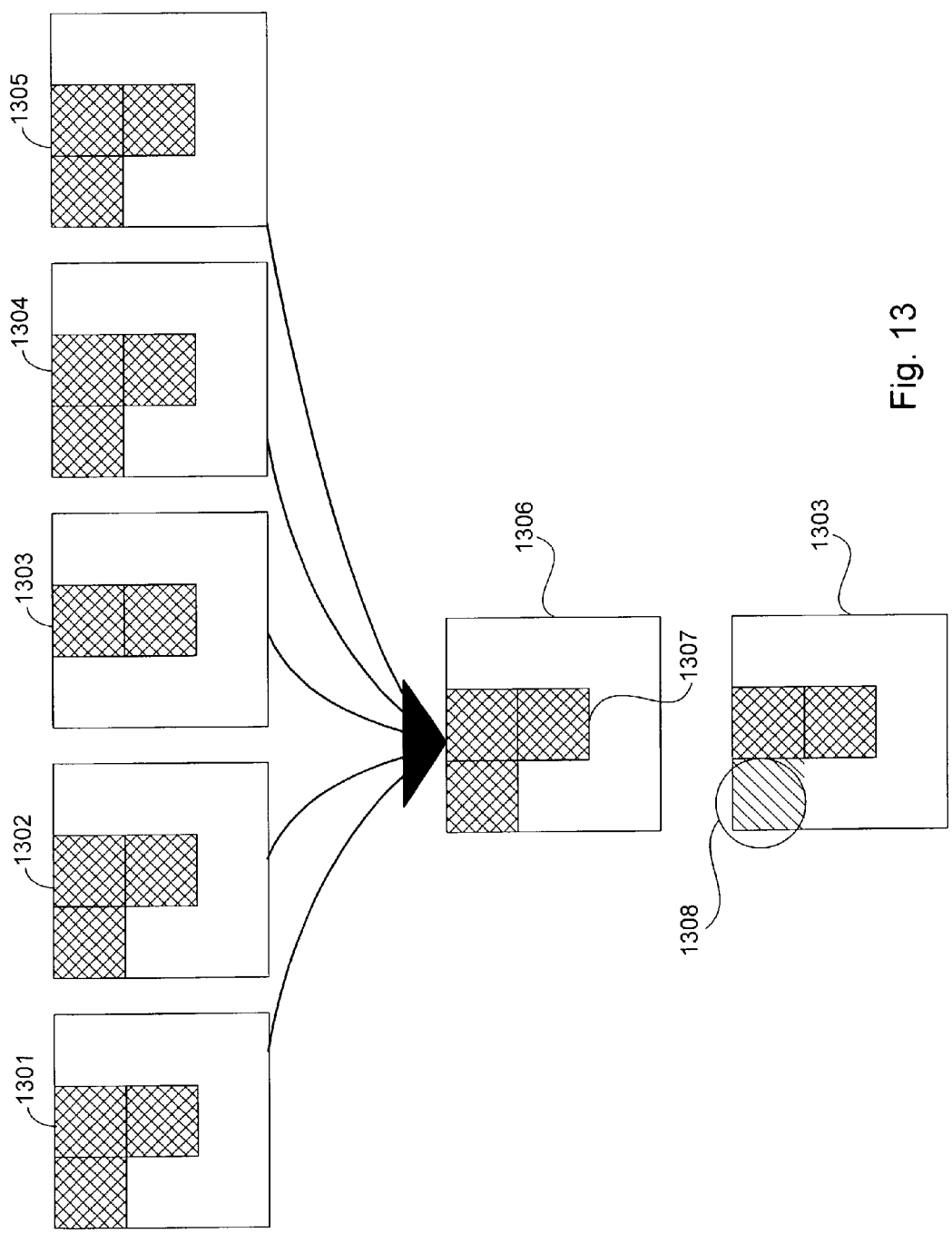
FIG. 13 is a simplified illustration depicting an embodiment for comparing light scattering images to identify defects in accordance with the principles of the present invention.

A simplified example of pattern comparison process used to locate and identify defects is depicted in FIG. 13. An inspection point at a first location on a first die is illuminated and forms a scattering pattern. A simplified nine pixel photo detector array produces a first sample image 1301 of this scattering pattern. Another inspection point at an analogous (equivalent) inspection point on a second die is illuminated and forms a second sample image 1302. Another inspection point at an analogous inspection point on a third die is illuminated and forms a third sample image 1303, and so on until sample images 1304 and 1305 are also formed. The sample images 1301, 1302, 1303, 1304, and 1305 are compared and a reference image 1306 is generated. For example, the reference image can be a pattern that the majority of the images conform to. Alternatively, a pixel-by-pixel analysis can be conducted wherein each pixel is classified as a "dark" pixel or a "light" pixel and then a comparison can be conducted to find pixels that are lighter than a pixel classified as a dark pixel. In this embodiment, a reference image 1306 is generated that includes a pattern of dark regions 1307 comprising three pixels. This image corresponds to the normal scattering pattern (in the absence of defects) exhibited by the subject inspection point. By comparing the reference image 1306 to the other sample images 1301, 1302, 1303, 1304, and 1305, it can be seen that the third sample image 1303 is different. The pixel 1308 of the third sample image 1303 is significantly lighter than that of the pattern of dark regions 1307 of the other sample images 1301, 1302, 1304, and 1305 (and reference image 1306). This indicates that there is a change in the light scattering from the inspection point on the third die. This scattering is detected by pixel 1308. This can indicate the presence of a defect at the selected inspection point on the third die. Thus, the selected inspection point on the third die is a defect candidate. Of course, there can be intermediate degrees of light cast on the pixels of the dark patterns. In such cases, a predetermined threshold level is set that defines when a pixel has become light enough to indicate a defect. This threshold level is adjustable in accordance with the needs of a process engineer. For example, when examining wafers that have not had many process steps performed on them or when used to inspect pattern masks, very low thresholds can be set making the process very sensitive to the presence of defects. Alternatively, when examining wafers that have had many layers formed on their surface (and therefore rather larger pattern variability due to accumulated errors in processing), higher thresholds can be set to reduce the incidence of false positive, but also reduce the sensitivity to the presence of defects. As indicated previously, in some implementations, all the pixels need not be compared. For example, in one implementation the darkest quartile of pixels of the reference image are selected as a subset for comparison. Thus, each comparison image compares an analogous subset of pixels to the selected subset of pixels of the reference image. Such an implementation is effective at improving defect detection in the presence of certain types of noise.

Because of the die-to-die comparison of each inspection point, the scattering effects due to the normal patterning of the inspection surface at the inspection point are automatically incorporated into all images of the same inspection point. Thus, the scattering patterns induced by patterning are adaptively filtered out by this invention. Additionally, if comparisons are conducted using only pixels that are darker than a predetermined value, then the comparison process functions similarly to that as used in Fourier filtering.

Such a technique does away with the need for the Fourier filtering techniques used in the prior art. However, such adaptive filtering is such that the deviations from the normal scattering patterns produced by the inspection points are still detectible. Thus, embodiments of the present invention are capable of detecting defects in patterned surfaces with a high degree of sensitivity.

Figure 14:
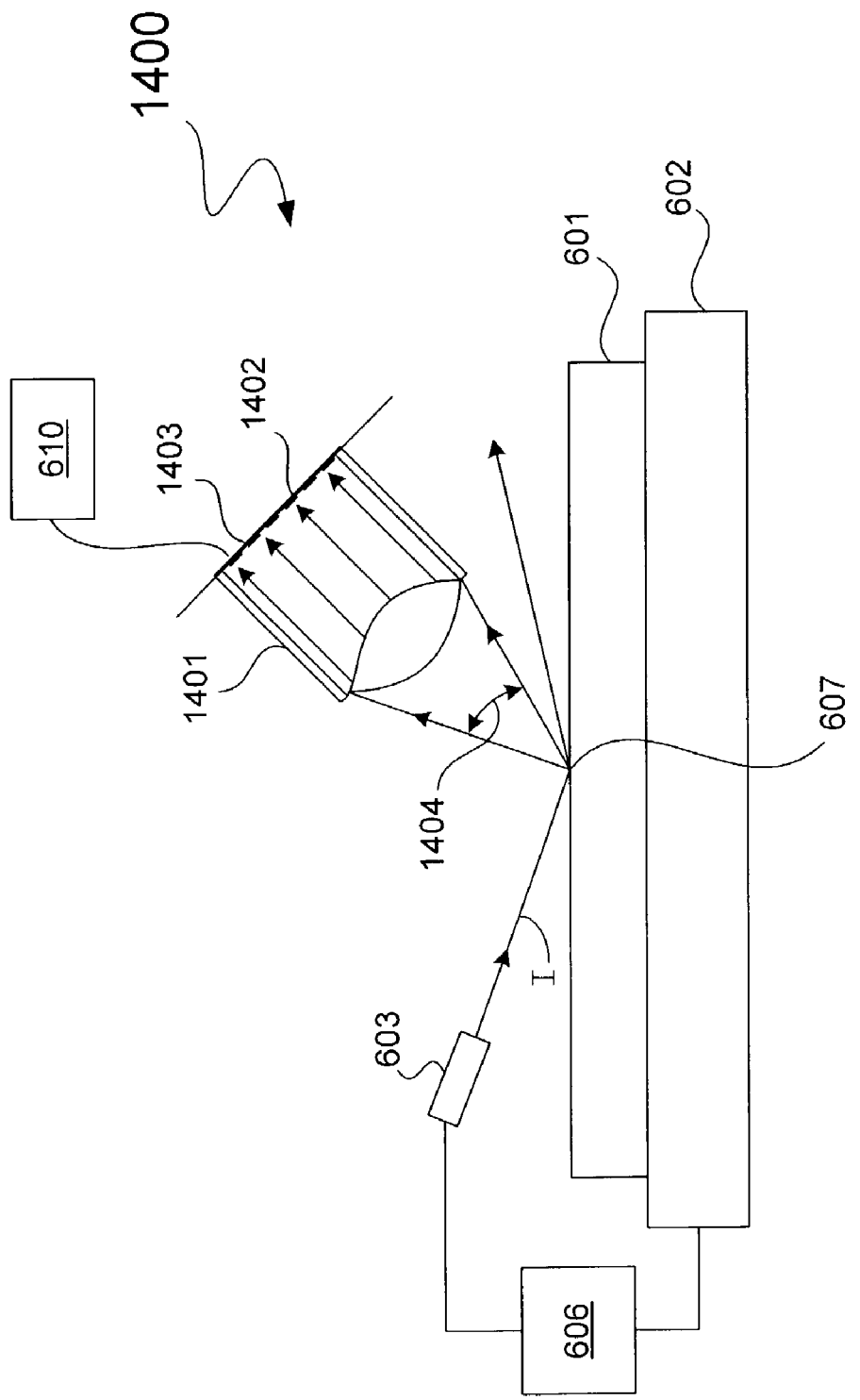
FIG. 14 is a cross-sectional view of an inspection device embodiment that includes a camera constructed in accordance with the principles of the present invention.

FIG. 14 is a simplified illustration of another embodiment of an inspection device constructed in accordance with the principles of the present invention. The device 1400 is designed to inspect desired portions of an inspection surface or work piece 601. As previously explained, work pieces 601 can include semiconductor wafers, pattern masks, and other inspection surfaces. A work piece 601 is positioned on a support 602, such as an electrostatic chuck or other commonly used support apparatus used for such purposes. An illumination source 603 is used to direct light beam I onto a specific inspection point 607 on the work piece 601. A suitably positioned camera 1401 receives the scattered light beams. The camera includes a photo detector array 1402 that receives the light scattered from the inspection point 607. Additionally, the device includes a scanning element 606 that moves the work piece 601 and light beam I relative to one another so that the beam I scans a desired path over the work piece 601 surface. The camera 1401 captures images of light scattering patterns generated as the beam I scans a desired path over the work piece 601 surface. The photo detector array 1402 is electrically connected to signal processing circuitry 610, which can receive image data, store images, and otherwise process such image data.

In the depicted embodiment, the illumination source 603 is a laser as described hereinabove. Also, as described hereinabove, scanning is accomplished using a scanning element 606.

In the depicted embodiment, the photosensitive elements of the photo detector array 1402 are arranged inside the camera along a detection surface 1403. As described above, the photo detector array 1402 can be formed of a number of light sensitive detector devices including, without limitation, photodiode arrays, photo multiplier tubes (PMT's), arrays of charge-coupled devices (CCD's), CMOS detector arrays, and a variety of other light sensing devices known to those having ordinary skill in the art. In the depicted embodiment, the detection surface 1403 is a Fourier plane. As with the previously described embodiments, the individual photosensitive elements of the photo detector array 1402 are each smaller than the solid angle subtended by the illumination beam, or the angular extent of the detector array 1402 should be much larger than the laser wavelength ($\lambda$)/spot size in both angular dimensions in order to have many independent samples of the scattering pattern. In one preferred implementation, the camera 1401 is arranged to admit light subtending a solid angle 1404 of greater than about 40° by 40° (a portion of said subtended solid angle 1404 extends directly into the page at an angle of 90° with the surface of the page).

In one preferred embodiment, the individual photosensor elements of the photo detector array 1402 are configured such that the photosensor elements subtend an angle of about: laser wavelength ($\lambda$)/spot size. For example, using a $\lambda$ of about 365µ and a spot size of 3µ, the photo sensor should subtend an angle of 0.365/3 radians (or about 7 degrees). As mentioned above, there is a trade off between sensitivity (lots of samples) and speed. In other implementations, a photosensor element of in the range of about 1.75° and 4° is suitable for a spot size of 3µ. Still other embodiments include photo sensors configured to subtend angles in the range of about 4° to about 12°. In one implementation, a 16×16 pixel Hamamatsu C4675 photo array is used.

Figure 15:
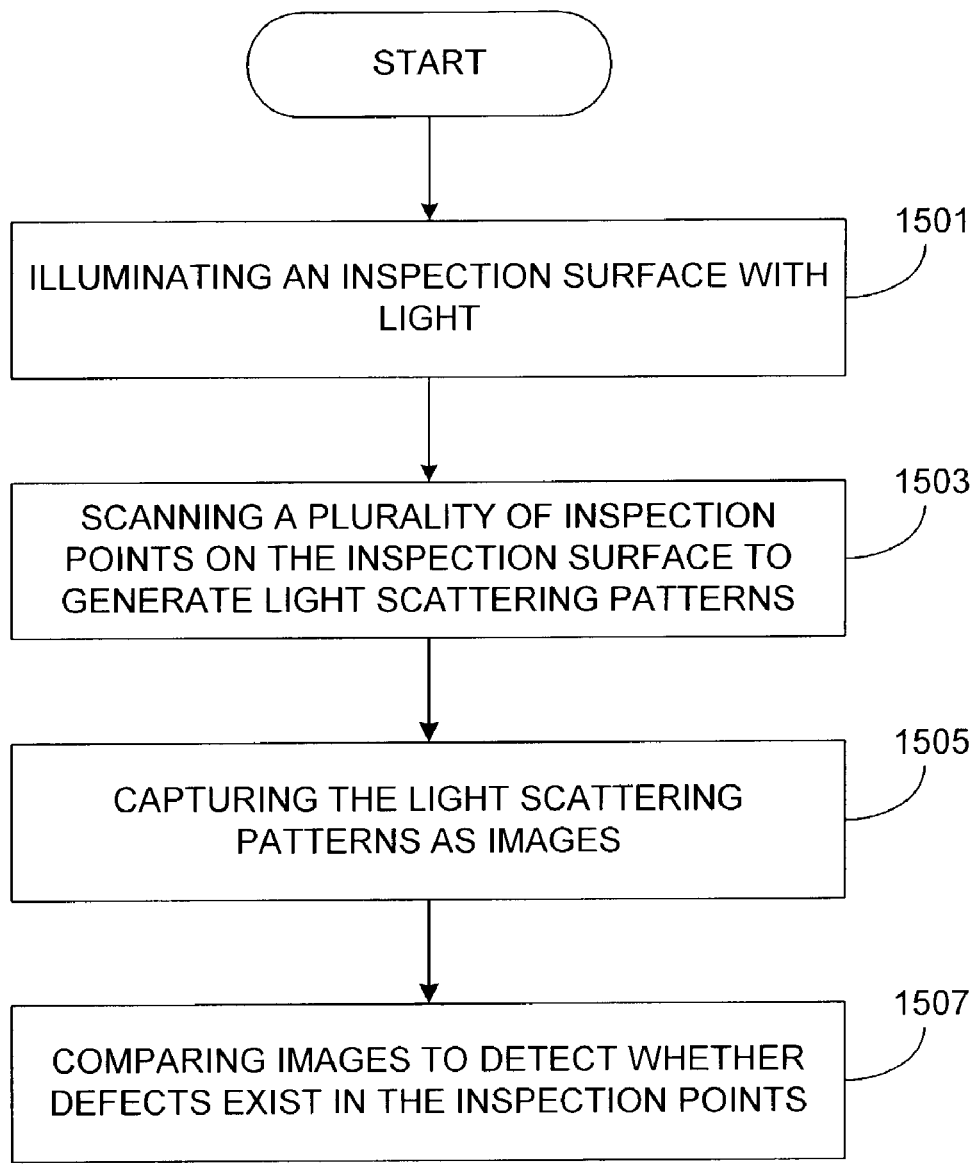
FIG. 15 is a flow diagram illustrating an embodiment of a process for inspecting a surface of a work piece in accordance with the principles of the present invention.

FIG. 15 is a flow diagram illustrating an embodiment of a process for inspecting a surface of a work piece in accordance with the principles of the present invention. Such a surface inspection method comprises illuminating an inspection surface with light (Step 1501). In one embodiment, the inspection surface is provided having a die pattern formed thereon. Suitable inspection surfaces include, but are not limited to, semiconductor wafers and mask patterns. The inspection surface is scanned with the light beam (Step 1503). Such scanning includes scanning a plurality of inspection points on the inspection surface, thereby generating light scattering patterns associated with the surface characteristics of the inspection points. The light scattering patterns are captured as images (Step 1505). Two-dimensional images of the light scattering patterns are captured at a light detection surface. Such images contain two-dimensional images of the intensity of the scattered light and the two-dimensional position of the scattered light generated at the inspection points. These capture light scattering patterns are stored as images along with the associated illumination location (inspection point). In this way these images can be compared at the same inspection point in multiple dies.

Images for the same inspection points can then be compared to detect whether defects exist in the inspection points (Step 1507). In one implementation, two-dimensional images for an inspection point are compared with a reference image that corresponds to the same inspection point. The comparison enables the identification of defects at the inspection point.

The present invention has been particularly shown and described with respect to certain preferred embodiments and specific features thereof. However, it should be noted that the above-described embodiments are intended to describe the principles of the invention, not limit its scope. Therefore, as is readily apparent to those of ordinary skill in the art, various changes and modifications in form and detail may be made without departing from the spirit and scope of the invention as set forth in the appended claims. Other embodiments and variations to the depicted embodiments will be apparent to those skilled in the art and may be made without departing from the spirit and scope of the invention as defined in the following claims. In particular, it is contemplated by the inventors, that photo detector arrays of the present invention are not limited to planar photo arrays. Photo detector arrays in accordance with the principles of the present invention can have a wide variety of shapes and can include photo detector arrays having curved surfaces. Further, reference in the claims to an element in the singular is not intended to mean "one and only one" unless explicitly stated, but rather, "one or more". Furthermore, the embodiments illustratively disclosed herein can be practiced without any element which is not specifically disclosed herein.

We claim:

1. A dark field surface inspection tool comprising:
   a) illumination source for directing a light beam onto an inspection point on a work piece, thereby generating a light scattering pattern associated with surface characteristics of the inspection point;
   b) scanning element that enables a plurality of inspection points on the work piece to be scanned, thereby generating light scattering patterns associated with each of the inspection points;
   c) photodetector array comprised of a plurality of photosensitive elements arranged to receive light from a light scattering pattern, so that a sample image of the light scattering pattern can be captured for each inspection point wherein the photosensitive elements of the photo detector array are arranged in a substantially hemispherical configuration relative to the inspection point; and
   d) circuitry for comparing the sample image with a reference image for the same inspection point, said comparison enabling the identification of defects at the inspection point wherein said comparison involves determining the darkest pixels in the reference image for a given reference point and comparing only the darkest pixels with corresponding pixels in the sample image to determine whether a defect is present at the inspection point of the sample image.

2. The dark field surface inspection tool of claim 1 wherein the work piece has a plurality of substantially similar semiconductor dies formed thereon;
   wherein the light beam illuminates an equivalent inspection point on a plurality semiconductor dies so that the photodetector array generates a plurality of sample images, each sample image corresponding to an equivalent inspection point on a different die; and
   wherein the circuitry is configured to compare the plurality of sample images to generate the reference image.

3. The dark field surface inspection tool of claim 1 wherein the reference image is generated using a model of the optical light scattering performance generated from a database model of the workpiece.

4. The dark field surface inspection tool of claim 1 wherein the photosensitive elements of the photo detector array are positioned such that the array subtends a solid angle of greater than about 40°×40°.

5. The dark field surface inspection tool of claim 1 wherein each of the photosensitive elements of the photo detector array are configured so that each photosensitive element subtends a solid angle that is related to the illumination solid angle of the light source.

6. The dark field surface inspection tool of claim 1 wherein the photosensitive elements of the photodetector array are arranged in a camera.

7. The dark field surface inspection tool of claim 6 wherein camera includes a photodetector array comprising 256 photosensitive elements.

8. The dark field surface inspection tool of claim 1 wherein each of the photosensitive elements of the photo detector array are configured so that each photosensitive element subtends a solid angle that is related to the wavelength of the laser ($\lambda$) and the spot size of the laser light dot.

9. The dark field surface inspection tool of claim 8 wherein the spot size of the laser is about 3µ in diameter and wherein each photosensitive element subtends a solid angle that is about 1.7° by 1.7° to about 4° by 4°.

10. A method of surface inspection comprising:
    providing an inspection surface;
    scanning an inspection point on the section surface with a light beam, thereby generating a light scattering pattern associated with surface characteristics of the inspection point;
    capturing, at a curved light detection surface, a two-dimensional image of the light scattering pattern generated by the inspection point such that the intensity of the scattered light and the two-dimensional position of the scattered light are captured as a sample image comprising light regions and dark regions wherein each light and dark region corresponds to a pixel of the sample image represented by a photosensitive element of the photodetector array; and
    comparing the sample image with a reference image that corresponds to the same inspection point, said comparison involving determining the darkest pixels in the reference image for a given reference point and comparing only the darkest pixels with corresponding pixels in the sample image enabling the identification of defects at the inspection point.

11. The method of claim 10 wherein comparing the sample image with the reference image includes generating the reference image using a model of the optical light scattering performance generated from a database model of the inspection surface.

12. The method of claim 10 wherein the defined as those pixels of the reference image having a light intensity value that falls below a pre-determined light intensity threshold.

13. The method of claim 12 wherein the pre-determined light intensity threshold is defined by light intensity values making up the darkest quartile of light intensity values in the reference image.

* * * * *

UNITED STATES PATENT AND TRADEMARK OFFICE
CERTIFICATE OF CORRECTION

| | | |
|---|---|---|
| PATENT NO. | : 7,106,432 B1 | Page 1 of 1 |
| APPLICATION NO. | : 10/315713 | |
| DATED | : September 12, 2006 | |
| INVENTOR(S) | : Mapoles et al. | |

It is certified that error appears in the above-identified patent and that said Letters Patent is hereby corrected as shown below:

In the Claims:

In line 5 of claim 5 (column 15, line 28) change "light source" to --illumination source--.

In line 2 of claim 8 (column 15, line 36) add --said illumination source comprises a laser and-- after "wherein".

In line 3 of claim 10 (column 16, line 5) change "section" to --inspection--.

In line 1 of claim 12 (column 16, line 33) add --darkest pixels in the reference image are--.

Signed and Sealed this

Nineteenth Day of June, 2007

JON W. DUDAS
*Director of the United States Patent and Trademark Office*